United States Patent
Shiina et al.

(10) Patent No.: US 10,494,673 B2
(45) Date of Patent: Dec. 3, 2019

(54) SIMPLE METHOD AND KIT FOR DNA TYPING OF HLA GENES BY HIGH-THROUGHPUT MASSIVELY PARALLEL SEQUENCER

(71) Applicant: GENODIVE PHARMA INC., Kanagawa (JP)

(72) Inventors: Takashi Shiina, Kanagawa (JP); Shingo Suzuki, Kanagawa (JP); Yuki Wada, Kanagawa (JP); Shigeki Mitsunaga, Kanagawa (JP); Hidetoshi Inoko, Kanagawa (JP)

(73) Assignee: GENODIVE PHARMA INC., Kanagawa (JP)

( * ) Notice: Subject to any disclaimer, the term of this patent is extended or adjusted under 35 U.S.C. 154(b) by 0 days.

(21) Appl. No.: 15/039,919

(22) PCT Filed: Nov. 27, 2014

(86) PCT No.: PCT/JP2014/081464
§ 371 (c)(1),
(2) Date: May 27, 2016

(87) PCT Pub. No.: WO2015/080226
PCT Pub. Date: Jun. 4, 2015

(65) Prior Publication Data
US 2017/0029885 A1  Feb. 2, 2017

(30) Foreign Application Priority Data
Nov. 27, 2013  (JP) .................... 2013-244624

(51) Int. Cl.
*C12Q 1/6881* (2018.01)
*C12N 15/00* (2006.01)

(52) U.S. Cl.
CPC ................. *C12Q 1/6881* (2013.01)

(58) Field of Classification Search
CPC ..................................... C12Q 1/6881
See application file for complete search history.

(56) References Cited

U.S. PATENT DOCUMENTS

| 2010/0086914 A1 | 4/2010 | Bentley et al. |
| 2014/0206005 A1 | 7/2014 | Shiina et al. |

(Continued)

FOREIGN PATENT DOCUMENTS

| CN | 101892317 A | 11/2010 |
| CN | 101962676 A | 2/2011 |

(Continued)

OTHER PUBLICATIONS

Shiina, T. et al., Super high resolution for single molecule-sequence-based typing of classical HLA loci at the 8-digit level using next generation sequencers, Tissue Antigens, vol. 80, pp. 305-318 (Year: 2012).*

(Continued)

*Primary Examiner* — Teresa E Strzelecka
(74) *Attorney, Agent, or Firm* — Pearne & Gordon LLP

(57) ABSTRACT

The present invention addresses the problem of providing a method and kit for the DNA profiling of HLA genes using a high-throughput massively parallel sequencer. The present invention pertains to a method for the DNA profiling of HLA genes, said method being characterized by including: (1) a step for preparing a primer set that anneals specifically to exon 4 and intron 1 and includes exon 2 and exon 3 of at least one target gene selected from the group consisting of HLA-DRB1, HLA-DRB3, HLA-DRB4, HLA-DRB5, HLA-DQB1 and HLA-DPB1 in the base sequence of the human genome; (2) a step for amplifying a sample (DNA) by PCR using the primer set; (3) a step for determining the base (Continued)

sequence of the amplified PCR product; and (4) a step for carrying out a homology search against a database.

1 Claim, 5 Drawing Sheets

Specification includes a Sequence Listing.

(56) References Cited

U.S. PATENT DOCUMENTS

| | | |
|---|---|---|
| 2016/0060695 A1 | 3/2016 | Shiina et al. |
| 2016/0208326 A1 | 7/2016 | Shiina et al. |

FOREIGN PATENT DOCUMENTS

| | | |
|---|---|---|
| EP | 0892069 A2 | 1/1999 |
| JP | H11-216000 A | 8/1999 |
| JP | 2011-500041 A | 1/2011 |
| WO | 0061795 A2 | 10/2000 |
| WO | 2005042764 A2 | 5/2005 |
| WO | 2009049889 A1 | 4/2009 |
| WO | 2010118865 A1 | 10/2010 |
| WO | 2013/011734 A1 | 1/2013 |
| WO | 2013011734 A1 | 1/2013 |
| WO | 2014/181854 A1 | 11/2014 |

OTHER PUBLICATIONS

Hosomichi, K. et al., Phase-defined complete sequencing of the HLA genes by next-generation sequencing, BMC Genomics, vol. 14:355, pp. 1-16 (Year: 2013).*
Wang, C. et al., High-throughput, high-fidelity HLA genotyping with deep sequencing, PNAS, vol. 109, pp. 8676-8681 (Year: 2012).*
Von Salome, J. et al., Full-length sequence analysis of the HLA-DRB1 locus suggests a recent origin of alleles, Immunogenetics, vol. 59, pp. 261-271 (Year: 2007).*
Dunn, P.P.J. et al., HLA-DQB1 sequencing-based typing using newly identified conserved nucleotide sequences in introns 1 and 2, Tissue Antigens, vol. 66, pp. 99-106 (Year: 2005).*
Lauterbach, N. et al., Full-length HLA-DPB1 diversity in multiple alleles of individuals from Caucasian, Black, or Oriental origin, Tissue Antigens, vol. 79, pp. 165-173 (Year: 2012).*
International Search Report dated Jul. 29, 2014 for PCT/JP2014/062433.
International Search Report dated Aug. 7, 2012 for PCT/JP2012/062743.
Bentley, et al. "High-resolution, high-throughput HLA genotyping by next-generation sequencing." Tissue antigens 74.5 (2009): 393-403.
Gabriel, et al. "Rapid high-throughput human leukocyte antigen typing by massively parallel pyrosequencing for high-resolution allele identification." Human immunology 70.11 (2009): 960-964.
Dunn, et al. "DNA sequencing as a tissue-typing tool." Pediatric Hematology: Methods and Protocols (2004): 233-246.
International Search Report dated Mar. 3, 2015 for PCT/JP2014/081464.
Extended European Search Report issued in application No. EP 14866271 dated May 12, 2017, 6 pages.
European Communication pursuant to Rule 164(1) EPC for Application No. 12814318.7.
"Experimental Medicine", vol. 27, No. 1, 2009 (Yodo-sha), Title page and p. 124 (brief description in English provided).
Hoglund, et al., Single pass very high resolution HLA genotyping by next generation sequencing with the 454 Life Sciences GS FLX and GS Junior. Tissue Antigens, Abstracts. 77(5), p. 465, (2011).
Holcomb et al. A multi-site study using high-resolution HLA genotyping by next generation sequencing. Tissue Antigens. 77(3), pp. 206-217, (2011).

Inoko, et al. "Transplantation/transfusion Examination", Kodan-sha Scientific, 2004, Title page and copyright page (brief description in English provided).
Genbank Accession No. L47206.1, "*Homo sapiens* MHC leukocyte antigen (HLA-A) gene, HLA-A*2401 allele, complete cds"; (GI: 6692988, available on Jan. 14, 2000, retrieved on Sep. 25, 2015).
Lind C., et al., "Next-generation sequencing: the solution for high-resolution, unambiguous human leukocyte antigen typing," Human Immunology, vol. 71, pp. 1033-1042 (2010).
Liu X. et al., Catalog of 162 single nucleotide 1-35 polymorphisms (SNPs) in a 4.7-kb region of the HLA-DP loci in southern Chinese ethnic groups, Journal of Human Genetics, vol. 49, pp. 73-79, (2004).
Lowe, et al., "A computer program for selection of oligonucleotide primers for polymerase chain reactions." Nucleic Acids Research 18.7: pp. 1757-1761; (1990).
Magor, et al., "Natural inactivation of a common HLA allele (A* 2402) has occurred on at least three separate occasions." The Journal of Immunology 158.11, pp. 5242-5250, (1997).
Moonsamy, et al. "High throughput HLA genotyping using 454 sequencing and the Fluidigm Access Array System for simplified amplicon library preparation," Tissue Antigens, vol. 81, No. 3, pp. 141-149, (2003).
Genbank Accession No. NT_007592.15 "*Homo sapiens* chromosome 6 genomic contig, GRCh37.p13 Primary Assembly"; (available Jun. 10, 2009, retrieved on Sep. 23, 2015).
Genbank Accession No. NG_029217.1, "*Homo sapiens* major histocompatibility complex, class I, A (HLA-A)"; (GI: 338827610, available Jun. 25, 2011, retrieved on Sep. 25, 2015).
Marsh SGE, et al., Nomenclature for Factors of the HLA System, Update to HLA Nomenclature, http://hla.alleles.org/nomenclature/naming_2010.html, pp. 1-3, (2010).
Ozaki et al., "SS-SBT-ho no Kaihatsu ( 1): HLA-DRB3/4/5 Primer no Kaihatsu to HLA11 Idenshiza nl Okeru PCR Joken no Toi tsuka", the 22nd Annual Meeting of the Japanese Society for Histocompatibility and Immunogenetics Shorokushu, Aug. 30, 2013 (Aug. 30, 2013), p. 64, A-4 (including brief description in English).
Ozaki, et al. "Jisedai Sequencer o Mochiita HLA-DRB1 Idenshi no Cho Kokaizodo DNA Typing (Super high resolution Single molecule-Sequence Based Typing; SS-SBT) Ho no Kaihatsu", MHC, 2012, vol. 19, No. 2, 211-221 (including English Abstract).
Von Salomé, et al., "Full-length sequence analysis of the HLA-DRB1 locus suggests a recent origin of alleles." Immunogenetics 59.4, pp. 261-271, (2007).
Seurynck, et al., Use of 3' and 5' 1-35, Untranslated Region Polymorphism of Class I HLA-B to Determine Full Length Nucleotide Sequences, Human Immunology, vol. 55, No. Supp. 1, p. 28, (1997).
Shiina. et al., Super high resolution for single molecule-sequence-based typing of classical HLA loci at the 8-digit level using next generation sequencers, Tissue Antigens, vol. 80, pp. 305-316, (2012).
Shiina et al., "HLA Kenkyu no Rinsho Oyo o Mezashita 8-keta Level HLA Typing-ho no Kaihatsu", MHC, vol. 19, No. 2 p. 133, (2012) (including brief description in English).
Shingo, et al. "Jisedai Sequencer o Mochiita HLA Class I Idenshi no Cho Kokaizodo DNA Typing (Super high resolution Single molecule-Sequence Based Typing; SS-SBT) Ho no Kaihatsu", MHC, vol. 19, No. 1, pp. 43-53, (2012) (including English Abstract).
Zhu, et al. "Analysis of the complete genomic sequence of HLA-A alleles in the Chinese Han population," International Journal of Immunogenetics 26, pp. 351-360, (2009).
Zhu, et al. Analysis for complete genomic sequence of HLA-B and HLA-C alleles in the Chinese Han population, International Journal of Immunogenetics, vol. 38, p. 281-284 (2011—published online).
Office action in related U.S. Appl. No. 14/233,909, dated Oct. 2, 2015.
Chinese Office Action dated Nov. 15, 2014 for Application No. 201280036108.5.
Kobrle et al., "New PCR and Sequencing Reagents for Sequence Based Typing of HLA-DRB1 Exon 2 and Exon 3," Abstract 165-P, Abstracts/Human Immunology 74 (2013) 51-173.

(56) References Cited

OTHER PUBLICATIONS

Office Action for corresponding Chinese Application No. 201480074262.0 dated Mar. 4, 2019, seven pages.

* cited by examiner

[fig.1]
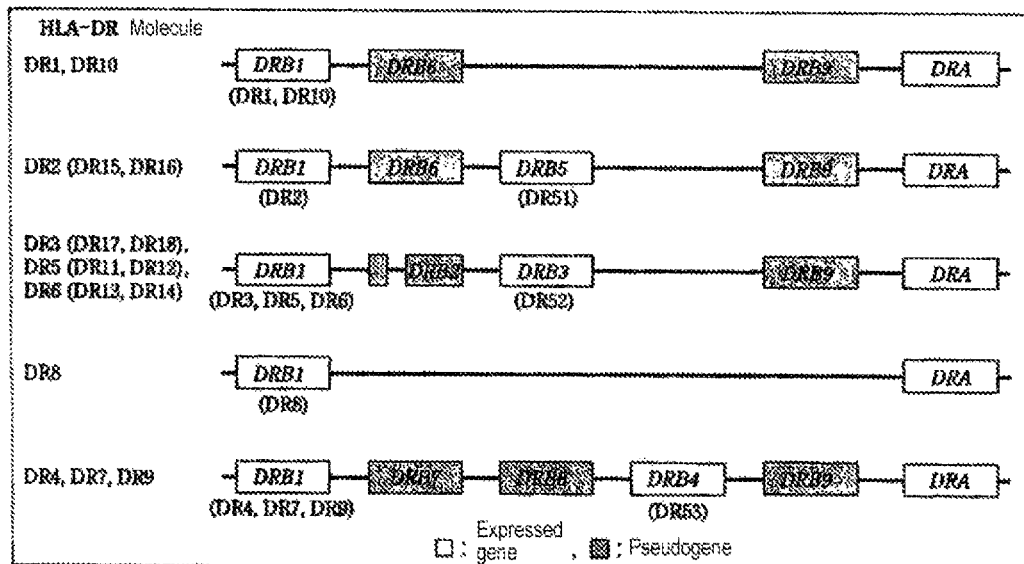
[fig.2]
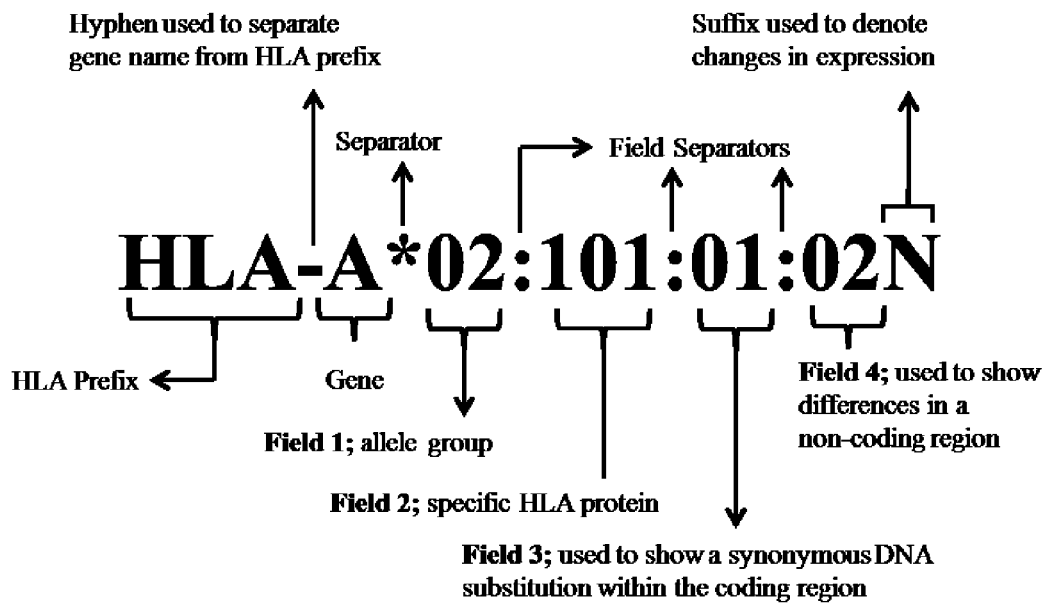

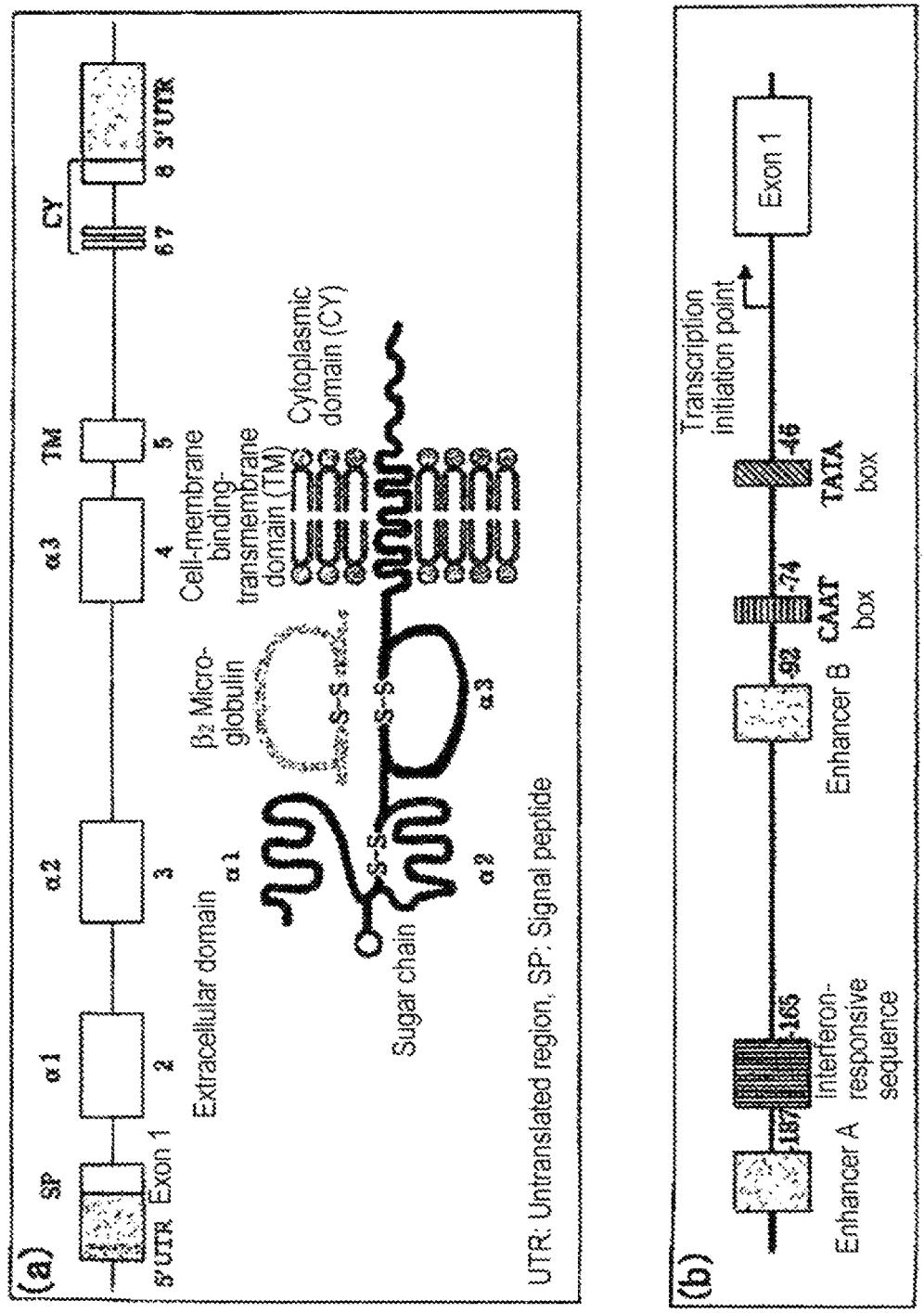
[fig.3]

[fig.4]
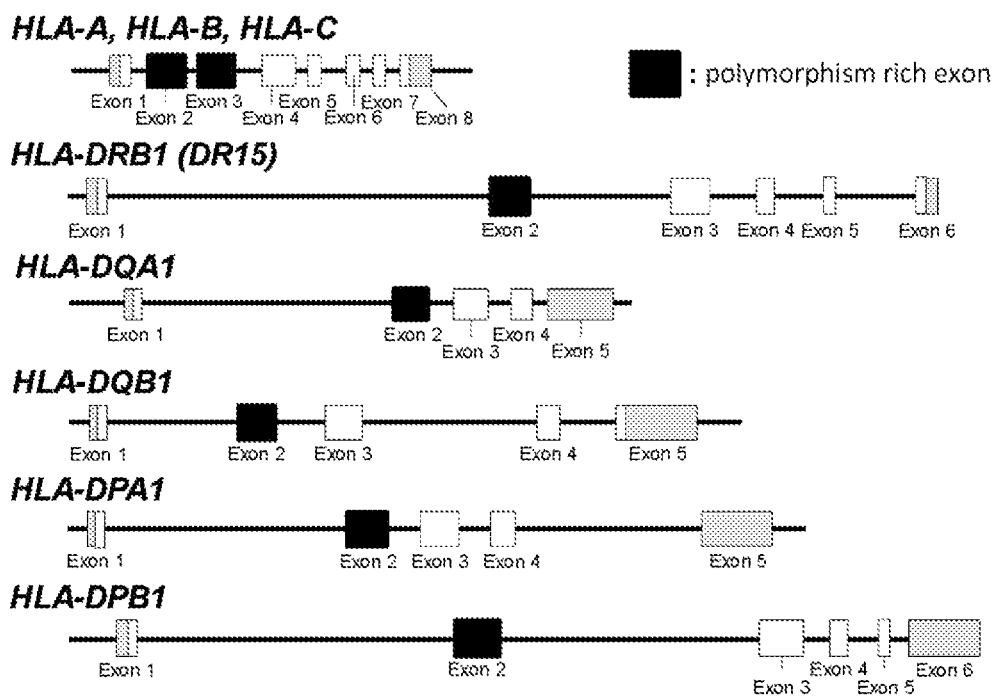
[fig.5]
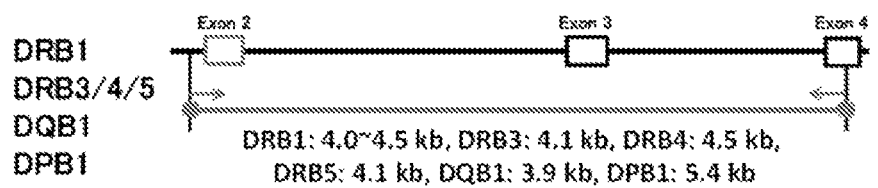

[fig.6]
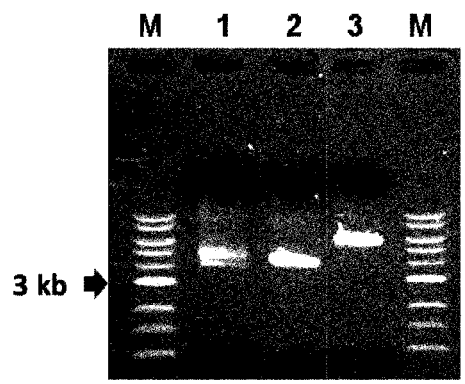
[fig.7]
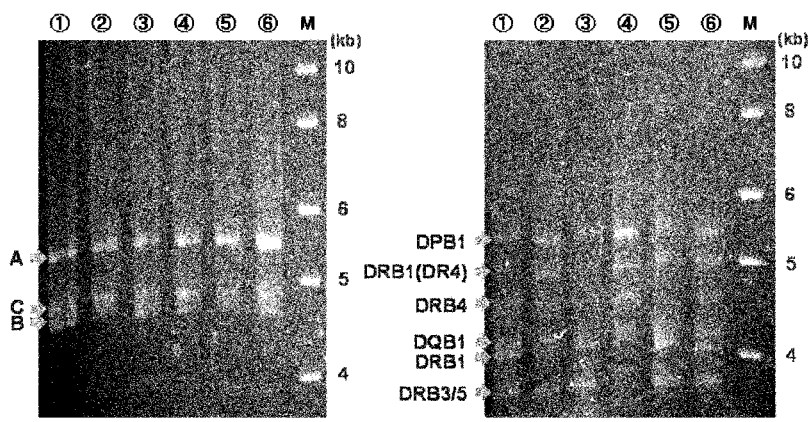

[fig.8]
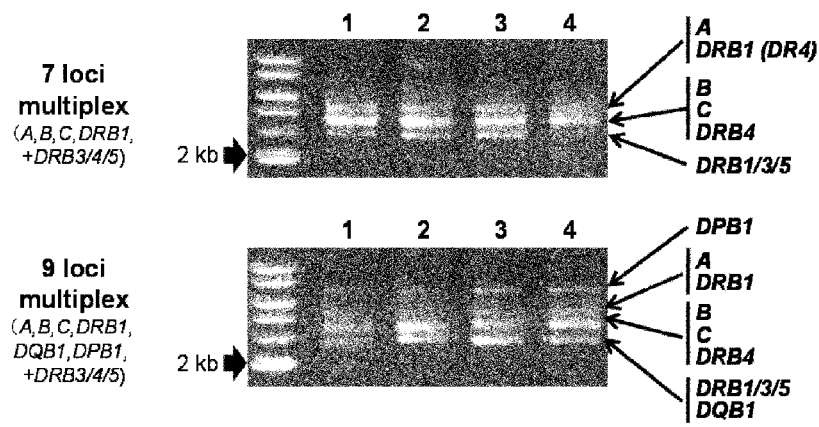

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 1
ttcactgctc ttwaagctcc cccag                                   25

<210> SEQ ID NO 2
<211> LENGTH: 23
<212> TYPE: DNA
<213> ORGANISM: Artificial Sequence
<220> FEATURE:
<223> OTHER INFORMATION: Synthesized Polynucleotide

<400> SEQUENCE: 2
ctctgtgcag attcrgaccg rgc                                     23

<210> SEQ ID NO 3
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 3
tgtaaaatca gcccgactgc ctcttc                                  26

<210> SEQ ID NO 4
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 4
gcaaaatcaa cccgactgcc tcttc                                   25

<210> SEQ ID NO 5
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 5
gggcagattc agaytgagcc ccta                                    24

<210> SEQ ID NO 6
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 6
tgctcgcccc tccctagtga t                                       21

<210> SEQ ID NO 7
<211> LENGTH: 29
<212> TYPE: DNA
<213> ORGANISM: Artificial Sequence

```
<220> FEATURE:
<223> OTHER INFORMATION: Synthesized Polynucleotide

<400> SEQUENCE: 7
tcaatgtctt actcygggca gaatcagac                                29

<210> SEQ ID NO 8
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 8
cagaaactca gagctaagga atgatggcaa at                            32

<210> SEQ ID NO 9
<211> LENGTH: 32
<212> TYPE: DNA
<213> ORGANISM: Artificial Sequence
<220> FEATURE:
<223> OTHER INFORMATION: Synthesized Polynucleotide

<400> SEQUENCE: 9
cagaaactca gagctatgga atgatggtaa at                            32

<210> SEQ ID NO 10
<211> LENGTH: 30
<212> TYPE: DNA
<213> ORGANISM: Artificial Sequence
<220> FEATURE:
<223> OTHER INFORMATION: Synthesized Polynucleotide

<400> SEQUENCE: 10
gcatataacc atcatcgtgt cccaaggttc                               30

<210> SEQ ID NO 11
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 11
ggttcccggt tgcaatagac agtaacaaa                                29

<210> SEQ ID NO 12
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 12
acgggtccaa tttcacagac aaatgt                                   26

<210> SEQ ID NO 13
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 13
acactgctta gatgtgcata gttcacgaa                                29
```

```
<210> SEQ ID NO 14
<211> LENGTH: 29
<212> TYPE: DNA
<213> ORGANISM: Artificial Sequence
<220> FEATURE:
<223> OTHER INFORMATION: Synthesized Polynucleotide

<400> SEQUENCE: 14
acactgctta gatgtgcata gttccggaa                                           29

<210> SEQ ID NO 15
<211> LENGTH: 40
<212> TYPE: DNA
<213> ORGANISM: Artificial Sequence
<220> FEATURE:
<223> OTHER INFORMATION: Synthesized Polynucleotide

<400> SEQUENCE: 15
gaacaattct agactatgga cccaatttta caaacaaata                               40

<210> SEQ ID NO 16
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 16
ctcagtgctc gcccctccct agtgat                                              26

<210> SEQ ID NO 17
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 17
gcacagtagc tttcgggaat tgacca                                              26
```

SIMPLE METHOD AND KIT FOR DNA TYPING OF HLA GENES BY HIGH-THROUGHPUT MASSIVELY PARALLEL SEQUENCER

TECHNICAL FIELD

The present invention relates to a method and a kit for DNA typing of HLA genes using a high throughput massive parallel sequencer.

BACKGROUND ART

The human leukocyte antigen (HLA) plays a central role in immunological discrimination between self and non-self. This discrimination is achieved when T cells recognize, via T cell receptors, HLA-peptide complexes presenting self- or non-self-derived peptides on HLAs. T cells recognize cells expressing, on the surface, HLA-peptide complexes presenting non-self (pathogenic microbes such as viruses and bacteria, or foreign antigens such as pollens)-derived peptides on self-HLAs, or cells expressing, on the surface, non-self HLA alleles that have entered the body through transplantation or transfusion, thereby causing activation of immunocytes or destroy of the presenting cells.

Such activation of immunocytes or destroy of the presenting cells causes a rejection response or graft versus host disease (GVHD) in transfusion, medical transplantation including bone marrow transplantation, or regenerative medicine using iPS cells or ES cells. In patients receiving frequent platelet transfusion, an antibody against a non-self HLA is produced and brings about a significant reduction in the efficacy of the platelet transfusion. In some cases of medication, a drug (and a peptide) bound with a particular HLA may be recognized as a foreign substance, causing a severe adverse drug reaction based mostly on an allergy response.

Accordingly, medical transplantation or regenerative medicine requires matching of HLAs between a patient and a donor. Transfusion of "HLA-compatible platelet" with HLA match is also necessary for platelet transfusion patients in which an anti-HLA antibody against a particular allele is produced. For adverse drug reactions, it is also important to examine HLAs before medication when the drug to be administered is reportedly related to a particular HLA allele. In actuality, package inserts of some drugs clearly states recommendation to examine HLAs. Peptide vaccine therapy of cancer also requires examining HLAs for predicting whether or not the peptide vaccine can bind to patient's HLAs.

As major HLAs, six types of antigens are known, namely, class I molecules (HLA-A, HLA-B and HLA-C), which are expressed in almost all cells, and class II molecules (HLA-DR, HLA-DQ and HLA-DP), which are expressed mainly in immune cells.

The HLA class I antigen consists of a highly polymorphic α chain and a substantially non-polymorphic β2-microglobulin; whereas the HLA class II antigen consists of a highly polymorphic β chain and a less polymorphic α chain. The α chains of class I molecules are encoded by HLA-A, HLA-B and HLA-C genes. The β chains of class II antigens are encoded by HLA-DRB1, HLA-DRB3, HLA-DRB4, HLA-DRB5, HLA-DQB1 and HLA-DPB1 genes, whereas the α chains are encoded by HLA-DRA1, HLA-DQA1 and HLA-DPA1 genes. In a gene level, in HLA class I antigens, exon 2 and exon 3 of a gene encoding an α chain are highly polymorphic; whereas, in HLA class II antigens, exon 2 of a gene encoding a β chain is highly polymorphic.

A gene region encoding an HLA is located on short arm of human chromosome 6 at 6p21.3. A class I region (HLA-A, HLA-C, HLA-B, etc.), a class III region and a class II region (HLA-DRA, HLA-DRB1, HLA-DQA1, HLA-DQB1, HLA-DPA1, HLA-DPB1, etc.) are arranged in this order from the telomere side toward the centromere side. Many genes are encoded at an extremely high density and association of these genes with transfusion, transplantation and various diseases has been reported. In the class III region, no HLA genes are present and genes of complement components and tumor necrosis factors (TNF), etc. are present.

In an HLA-DRB gene region encoding a β chain of an HLA-DR antigen, it has been confirmed that 5 types of structural polymorphisms are present. In DR1 type and DR10 type, pseudogenes such as HLA-DRB6 and HLA-DRB9 in addition to HLA-DRB1 are located on the same chromosome. In DR2 type, an HLA-DRB5 (DR51) gene and pseudogenes such as HLA-DRB6 and HLA-DRB9 in addition to HLA-DRB1 are located on the same chromosome. In DR3, DR5 and DR6 types, an HLA-DRB3 (DR52) gene and pseudogenes such as HLA-DRB2 and HLA-DRB9 in addition to HLA-DRB1 are located on the same chromosome. In DR4, DR7 and DR9 types, an HLA-DRB4 (DR53) gene and pseudogenes such as HLA-DRB7, HLA-DRB8 and HLA-DRB9 in addition to HLA-DRB1 are located on the same chromosome. In contrast to these, in DR8 type, no HLA-DRB genes except HLA-DRB1 are located on the same chromosome (see FIG. 1).

In the exon of each allele, a plurality of regions exhibiting polymorphism are present. In many cases, a nucleotide sequence (amino acid sequence) present in a certain polymorphic region is commonly present in a plurality of alleles. In short, each HLA allele is specified by a plurality of polymorphic regions in combination. In an HLA class II antigen, not only a polymorphic region in the exon but also exon 2 or exon 3 having the same nucleotide sequence is sometimes commonly present in a plurality of alleles.

Since a highly polymorphic region is present in an HLA, the number of types of alleles is known to be extremely large and notation of them has been defined: i.e., a first field (two-digit level) is for discrimination of serologic HLA types, a second field (4-digit level) is for discrimination of alleles having an amino acid substitution in the same serologic HLA type, a third field (6-digit level) is for discrimination of alleles having a base substitution not accompanying an amino acid mutation and a fourth field (8-digit level) is for discrimination of alleles having a base substitution in an intron, which is out of the genetic region encoding an HLA molecule (see FIG. 2).

In various medical cases, examination of HLA alleles (DNA typing of HLA genes) is important. However, a SBT (sequence-based typing) method or a Luminex method (PCR-sequence-specific oligonucleotide probes (SSOP)-Luminex method), which has heretofore been frequently used, cannot easily determine whether polymorphic regions are in a cis-configuration (on the same chromosome) or in a trans-configuration (on different chromosomes), if a plurality of different polymorphic regions are present between alleles. Therefore, the alleles were sometimes unable to be accurately determined due to the occurrence of so-called phase ambiguity.

Hence, we developed a method capable of eliminating phase ambiguity by using a next generation sequencer (high throughput massive parallel sequencer). In this method, however, typing of fragmented DNAs in a poor state of preservation was sometimes not easily performed because a long region containing 3'UTR was amplified from a promoter region. Particularly, an HLA class II gene has long intron 1, which requires amplifying a region about twice longer than that of a class I gene. Therefore, typing of DNA fragment samples was not easily performed.

RELATED ART DOCUMENT

Patent Document

Patent Document 1: JP H11-216000 A

Non Patent Document

Non Patent Document 1: Lind C. et al., Human Immunology, Vol. 71, Pages 1033-1042 (2010)
Non Patent Document 2: Shiina T. et al., Tissue Antigens, Vol. 80, Pages 305-316 (2012)

SUMMARY OF THE INVENTION

Problems to be Solved by the Invention

An object of the present invention is to provide a method, a primer set and a kit for DNA typing of HLA genes using a high throughput massive parallel sequencer, which attain typing even in the case of using fragmented DNA samples in a poor state of preservation and are capable of simultaneously PCR amplifying HLA genes using a plurality of primer sets under the same PCR conditions.

Means for Solving the Problems

The present inventors developed a system in which a region from exon 2 to a portion of exon 4 of an HLA class II gene, which is highly polymorphic so as to bring about a difference between alleles and encodes an extracellular domain recognizable by an antibody or a T cell receptor, is amplified and subjected to DNA typing using a next generation sequencer.

Specifically, the present inventors came up with the new idea of newly designing each of PCR primers capable of simultaneously amplifying HLA-DRB1, HLA-DRB3, HLA-DRB4 and HLA-DRB5 genes, which are HLA class II genes, and PCR primers capable of specifically amplifying HLA-DQB1 and HLA-DPB1 genes, setting preferable PCR conditions, and using a high throughput massive parallel sequencing technique. As a result of performing diligent research based on this idea in order to solve the above-described problems, the present inventors completed the present invention.

In other words, the present invention provides a method for DNA typing of an HLA gene, including the following steps:
(1) a step of preparing a set of primers which anneal specifically to an intron 1 region containing exon 2 and exon 3 and an exon 4 region, respectively, of at least one target gene selected from the group consisting of HLA-DRB1, HLA-DRB3, HLA-DRB4, HLA-DRB5, HLA-DQB1 and HLA-DPB1 genes in a human genome sequence;
(2) a step of PCR amplifying a test sample (DNA) using the set of primers;
(3) a step of determining the nucleotide sequence of the PCR amplified product; and
(4) a step of carrying out a homology search within a database.

In one embodiment the target gene is at least one gene selected from the group consisting of HLA-DRB1, HLA-DRB3, HLA-DRB4 and HLA-DRB5 genes and the set of primers is oligonucleotides having nucleotide sequences as shown in SEQ ID NOs: 1 and 2, respectively. In an alternative embodiment, the target gene is an HLA-DQB1 gene and the set of primers is oligonucleotides having nucleotide sequences as shown in any one of SEQ ID NOs: 3 and 4, or both, and SEQ ID NO: 5, respectively. In a further alternative embodiment, the target gene is an HLA-DPB1 gene and the set of primers is oligonucleotides having nucleotide sequences as shown in SEQ ID NOs: 6 and 7, respectively.

In another aspect, the present invention relates to a primer set capable of simultaneously PCR amplifying a DNA region including exon 2 and exon 3 of at least one gene selected from the group consisting of HLA-DRB1, HLA-DRB3, HLA-DRB4 and HLA-DRB5 genes. In one embodiment, the present invention provides a primer set for DNA typing of at least one gene selected from the group consisting of HLA-DRB1, HLA-DRB3, HLA-DRB4 and HLA-DRB5 genes, including oligonucleotides having nucleotide sequences as shown in SEQ ID NOs: 1 and 2, respectively. In an alternative embodiment, the present invention provides a primer set for DNA typing of an HLA-DQB1 gene, including oligonucleotides having nucleotide sequences as shown in any one of SEQ ID NOs: 3 and 4, or both, and SEQ ID NO: 5, respectively. In a further alternative embodiment, the present invention provides a primer set for DNA typing of an HLA-DPB1 gene, including oligonucleotides having nucleotide sequences as shown in SEQ ID NOs: 6 and 7, respectively.

Effects of the Invention

The method of the present invention, since it provides all nucleotide sequences required for DNA typing of an HLA gene from a single molecule, is an ultimate DNA typing method in which phase ambiguity due to unclear cis/trans positional relationship is eliminated. Owing to this, a region from exon 2 to a portion of exon 4 of an HLA class II gene, which is highly polymorphic and encodes an extracellular domain recognizable by an antibody or a T cell receptor can be amplified and DNA typing with a next generation sequencer is realized.

Furthermore, since an amplification region is shortened, DNA typing of an HLA gene can be relatively easily performed even in the case of using DNA samples in a poor state of preservation. In addition, the length of the region to be amplified is nearly equal to an already published amplification region of a class I gene. Use of the primer sets of the present invention enables a plurality of HLA genes to be simultaneously PCR amplified under the same PCR conditions and can therefore shorten the time required for PCR. Moreover, the data size is also reduced and the time required for data analysis is therefore also shortened.

BRIEF DESCRIPTION OF DRAWINGS

FIG. 1 A diagram showing an HLA-DR gene region, cited from "Transplantation/transfusion Examination", supervised by Hidetoshi Inoko, Takehiko Sasazuki and Takeo Juuji, Kodan-sha Scientific, 2004, page 48.
FIG. 2 A diagram showing a classification of HLA alleles, cited from the IMGT-HLA database (www.ebi.ac.uk/ipd/imgt/hla/).

FIG. 3 (a) A diagram showing the relationship between the structure of an HLA class I gene and the structure of an HLA class I molecule; and (b) A diagram showing the structure of a promoter region of an HLA class I gene, cited from "Transplantation/transfusion Examination", supervised by Hidetoshi Inoko, Takehiko Sasazuki and Takeo Juuji, Kodan-sha Scientific, 2004, page 35.

FIG. 4 A schematic diagram showing the structure of each HLA gene.

FIG. 5 A diagram showing the lengths of PCR products estimated from the positions of primers designed on an HLA class II gene and reference sequences.

FIG. 6 An agarose gel electrophoretic pattern obtained using newly developed primers.

FIG. 7 An agarose gel electrophoretic pattern obtained by a multiplex PCR.

FIG. 8 An agarose gel electrophoretic pattern obtained by a multiplex PCR.

MODES FOR CARRYING OUT THE INVENTION

Now, the DNA typing method of the present invention will be more specifically described step by step.

(1) Step of Preparing a Primer Set

In the DNA typing method of the present invention, first, a set of primers which anneal specifically to intron 1 including exon 2 and exon 3 and exon 4, respectively, of at least one target gene selected from the group consisting of HLA-DRB1, HLA-DRB3, HLA-DRB4, HLA-DRB5, HLA-DQB1 and HLA-DPB1 genes in a human genome sequence and can anneal under the same conditions is prepared.

The genome sequence of human chromosome 6 (6p21.3) in which an HLA gene is present has been already elucidated and association between the gene structure and the structure of an expression product (HLA antigen) has been known (see FIGS. 3 and 4).

In the present invention, a set of primers which can comprehensively PCR amplify regions including exon 2 and exon 3 of classic class II antigens (HLA-DRB1, HLA-DRB3, HLA-DRB4, HLA-DRB5, HLA-DQB1 and HLA-DPB1) is prepared (see FIG. 5), and PCR products obtained by PCR amplification using the set of primers are subjected to high throughput sequencing (described later). Therefore, uncertainty such as phase ambiguity can be eliminated and the presence or absence of a null allele can be accurately detected.

In Table 1, SEQ ID NOs: 1 and 2 represent a set of PCR primers specifically amplifying an HLA-DRB1 gene, an HLA-DRB3 gene, an HLA-DRB4 gene, and an HLA-DRB5 gene, which are β chains of MHC class II. These primers of the set are nucleotide sequences located at positions, which correspond to the upstream and downstream of exon 2 and exon 3 of each of an HLA-DRB1 gene and an HLA-DRB5 gene in a human genome sequence (Reference sequence: hg19), an HLA-DRB1 gene and an HLA-DRB3 gene in a human genome sequence (Reference sequence: 6_cox_hap2) and an HLA-DRB1 gene and an HLA-DRB4 gene in a human genome sequence (Reference sequence: mann_hap4), and sandwich these exons.

SEQ ID NO: 1 has a nucleotide sequence corresponding to the 32552643rd position to the 32552667th position and the 32490446th position to the 32490470th position in a human genome sequence (Reference sequence: hg19), the 4003862nd position to the 4003886th position and the 3939870th position to the 3939894th position in a human genome sequence (Reference sequence: 6_cox_hap2) and the 4000197th position to the 4000221st position and the 3851785th position to the 3851809th position in a human genome sequence (Reference sequence: mann_hap4).

SEQ ID NO: 2 has a complementary nucleotide sequence to a nucleotide sequence corresponding to the 32548609th position to the 32548631st position and the 32486419th position to the 32486441st position in a human genome sequence (Reference sequence: hg19), the 3999861st position to the 3999883rd position and the 3935840th position to the 3935862nd position in a human genome sequence (Reference sequence: 6_cox_hap2) and the 3996203rd position to the 3996225th position and the 3847267th position to the 3847289th position in a human genome sequence (Reference sequence: mann_hap4).

The length of a PCR product obtained by using this primer set is estimated from the reference sequence as about 4,000 to about 4,500 bases (bp).

In Table 1, SEQ ID NOs: 3 to 5 represent a set of PCR primers specifically amplifying an HLA-DQB1 gene, which is a β chain of MHC class II. These primers of the set are nucleotide sequences located at positions, which correspond to the upstream and downstream of exon 2 and exon 3 of an HLA-DQB1 gene and sandwich these exons, in a human genome sequence (Reference sequence: hg19).

SEQ ID NO: 3 has a nucleotide sequence corresponding to the 32633103rd position to the 32633128th position in a human genome sequence (Reference sequence: hg19).

SEQ ID NO: 4 has a nucleotide sequence corresponding to the 32633103rd position to the 32633127th position in a human genome sequence (Reference sequence: hg19).

SEQ ID NO: 5 has a complementary nucleotide sequence to a nucleotide sequence corresponding to the 32629214th position to the 32629237th position in a human genome sequence (Reference sequence: hg19).

The length of a PCR product obtained by using this primer set is estimated from the reference sequence as about 3,900 bases (bp).

In Table 1, SEQ ID NOs: 6 and 7 represent a set of PCR primers specifically amplifying an HLA-DPB1 gene, which is a β chain of MHC class II. These primers of the set are nucleotide sequences located at positions, which correspond to the upstream and downstream of exon 2 and exon 3 of an HLA-DPB1 gene and sandwich these exons, in a human genome sequence (Reference sequence: hg19).

SEQ ID NO: 6 has a nucleotide sequence corresponding to the 33048187th position to the 33048207th position in a human genome sequence (Reference sequence: hg19).

SEQ ID NO: 7 has a complementary nucleotide sequence to a nucleotide sequence corresponding to the 33053563rd position to the 33053591st position in a human genome sequence (Reference sequence: hg19).

The length of a PCR product obtained by using this primer set is estimated from the reference sequence as about 5,400 bases (bp).

These primers can be prepared by a method routinely used in this field. Furthermore, the sets of primers described in Table 1 are the most preferable examples. In the method of the present invention, any set of primers can be used as long as the set of primers is a set of a sense primer and an anti-sense primer capable of annealing to the positions, which correspond to the upstream and downstream of exon 2 and exon 3 of each HLA gene and sandwich these exons.

Further, in the present specification, even if primers correspond to the same region within the reference sequence, a separate sequence ID number is assigned to each primer as long as they differ in the nucleotides. The difference in the nucleotide is due to a polymorphism.

TABLE 1

| HLA class II gene | Name of primer | Length of primer (mer) | Primer sequence (5'-3') | SEQ ID NO | Estimated length of PCR product based on the reference sequence (bp) |
|---|---|---|---|---|---|
| HLA-DRB1 | DRB1-short-F201 | 25 | TTCACTGCTCTTWAAGCTC CCCCAG | 1 | 4,059 (DRB1) |
| HLA-DRB3 |  |  |  |  | 4,055 (cox:DRB3) |
| HLA-DRB4 | DRB1-short-R102 | 23 | CTCTGTGCAGATTCRGACC GRGC | 2 | 4,543 (mann:DRB4) |
| hLA-DRB5 |  |  |  |  | 4,052 (DRB5) |
| HLA-DQB1 | DQB1-short-F1.1 | 26 | TGTAAAATCAGCCCGACTG CCTCTTC | 3 | 3,915 |
|  | DQB1-short-F1.2 | 25 | GCAAAATCAACCCGACTGC CTCTTC | 4 |  |
|  | DQB1-short-R1 | 24 | GGGCAGATTCAGAYTGAGC CCCTA | 5 |  |
| HLA-DPB1 | DPB1-short-F1 | 21 | TGCTCGCCCCTCCCTAGTG AT | 6 | 5,405 |
|  | DPB1-short-R1 | 29 | TCAATGTCTTACTCYGGGC AGAATCAGAC | 7 |  |

Also, in the present invention, a set of primers for PCR of a region including exon 2 and exon 3 known to be highly polymorphic in each of genes of HLA-A, HLA-B and HLA-C, which are classic class I antigens, can be used in combination with the set of primers specific for the classic class II antigens. The set of primers specific for each of HLA-A, HLA-B and HLA-C genes can be exemplified as follows.

In Table 2, SEQ ID NOs: 8 to 10 represent a set of PCR primers specifically amplifying an HLA-A gene, which is an α chain of MHC class I. These primers of the set are nucleotide sequences located at positions, which correspond to the upstream and downstream of all regions of an HLA-A gene (including promoter, exons and introns) and sandwich the all regions, in a human genome sequence (Reference sequence: hg19).

SEQ ID NO: 8 or 9 has a nucleotide sequence corresponding to the 29909483rd position to the 29909514th position in a human genome sequence (Reference sequence: hg19).

SEQ ID NO: 10 has a complementary nucleotide sequence to a nucleotide sequence corresponding to the 29914925th position to the 29914954th position in a human genome sequence (Reference sequence: hg19).

The length of a PCR product obtained by using this primer set is estimated from the reference sequence as about 5,500 bases (bp).

In Table 2, SEQ ID NOs: 11 and 12 represent a set of PCR primers specifically amplifying an HLA-B gene, which is an α chain of MHC class I. These primers of the set are nucleotide sequences located at positions, which correspond to the upstream and downstream of all regions of an HLA-B gene (including promoter, exons and introns) and sandwich the all regions, in a human genome sequence (Reference sequence: hg19).

SEQ ID NO: 11 has a complementary nucleotide sequence to a nucleotide sequence corresponding to the 31325796th position to the 31325824th position in a human genome sequence (Reference sequence: hg19).

SEQ ID NO: 12 has a nucleotide sequence corresponding to the 31321210th position to the 31321235th position in a human genome sequence (Reference sequence: hg19).

The length of a PCR product obtained by using this primer set is estimated from the reference sequence as about 4,600 bases (bp).

In Table 2, SEQ ID NOs: 13 to 15 represent a set of PCR primers specifically amplifying an HLA-C gene, which is an α chain of MHC class I. These primers of the set are nucleotide sequences located at positions, which correspond to the upstream and downstream of all regions of an HLA-C gene (including promoter, exons and introns) and sandwich the all regions, in a human genome sequence (Reference sequence: hg19).

SEQ ID NO: 13 or 14 has a complementary nucleotide sequence to a nucleotide sequence corresponding to the 31240868th position to the 31240896th position in a human genome sequence (Reference sequence: hg19).

SEQ ID NO: 15 has a nucleotide sequence corresponding to the 31236075th position to the 31236114th position in a human genome sequence (Reference sequence: hg19).

The length of a PCR product obtained by using this primer set is estimated from the reference sequence as about 4,800 bases (bp).

TABLE 2

| HLA class I gene | Name of primer | Length of primer (mer) | Primer sequence (5'-3') | SEQ ID NO | Estimated length of PCR product based on the reference sequence (hg19) (bp) |
|---|---|---|---|---|---|
| HLA-A | A_F1.4 | 32 | CAGAAACTCAGAGCTAAGG AATGATGGTAAAT | 8 | 5,472 |
|  | A_F2.4 | 32 | CAGAAACTCAGAGCTATGG AATGATGGTAAAT | 9 |  |
|  | A_R1.2 | 30 | GCATATAACCATCATCGTG TCCCAAGGTTC | 10 |  |

TABLE 2-continued

| HLA class I gene | Name of primer | Length of primer (mer) | Primer sequence (5'-3') | SEQ ID NO | Estimated length of PCR product based on the reference sequence (hg19)(bp) |
|---|---|---|---|---|---|
| HLA-B | B_F1.4 | 29 | GGTTCCGGTTGCAATAGACAGTAACAAA | 11 | 4,615 |
|  | B_R1.2 | 26 | ACGGGTCCAATTTCACAGACAAATGT | 12 |  |
| HLA-C | C_F1.4 | 29 | ACACTGCTTAGATGTGCATAGTTCACGAA | 13 | 4,822 |
|  | C_F2.4 | 29 | ACACTGCTTAGATGTGCATAGTTCCGGAA | 14 |  |
|  | C_R1.16 | 40 | GAACAATTCTAGACTATGGACCCAATTTTACAAACAAATA | 15 |  |

One or two or more sets of primers described in the present specification may be used in a single container for PCR amplifying each HLA gene by, for example, a multiplex PCR method.

(2) Step of PCR Amplification

In the method of the present invention, a test sample (DNA) is amplified by a PCR method using the set of primers prepared in the above step (1).

The PCR amplification reaction is performed in accordance with a general protocol and more specifically, as follows.

1. DNA is extracted from a test sample depending upon the form of the sample.
2. The DNA extracted is quantified and the concentrations of primers are appropriately set to prepare the reaction solution.
3. Reaction conditions are set and a PCR is performed. For example:
Thermal denaturation step (usually 92 to 98° C.)
Annealing step (usually 55 to 72° C.)
Extension step (usually 65 to 80° C.)

In the method of the present invention, the temperature of the annealing step and the extension step is set preferably at about 65 to 70° C., more preferably at 65 to 68° C. Owing to the annealing and extension at about 65 to 70° C., HLA alleles can be produced at the equivalent ratio (uniformly).

4. The obtained PCR product is purified and subjected to the following nucleotide sequencing step.

The enzyme (DNA polymerase) used in the present invention is not particularly limited and may be commercial products. Examples can include PrimeSTAR® GXL DNA Polymerase, Tks Gflex® DNA Polymerase and TaKaRa LA Taq® (manufactured by TaKaRa Bio Inc.).

(3) Step of Nucleotide Sequencing

Next, the nucleotide sequence of the PCR product (amplified DNA) produced in the above step (2) is determined. The step is preferably performed by a technique called high throughput sequencing (or ultrahigh sequencing, a massive parallel sequencing). With respect to the high throughput sequencing, see, for example, "Experimental Medicine", Vol. 27, No. 1, 2009 (Yodo-sha).

A high throughput massive parallel sequencer includes a 454 GS system of Roche, a genome sequencer Ion Torrent PGM™ system by Life Technologies Corporation and MiSeq system by illumina, Inc., etc. In the present specification, a sequencing method which is employed in a 454 GS system of Roche will be described below.

1. The PCR product obtained in the above step (2) is broken up by a nebulizer into fragments of about 500 bases.
2. To an end of each of the DNA fragments, a DNA adaptor is attached.
3. DNA fragments attached with a DNA adaptor are dissociated into single stranded DNA fragments, which are allowed to bind to beads via the adaptor. The obtained beads are encompassed and taken in a water-in-oil emulsion. As a result, a micro-reactor environment containing a single DNA fragment bound to a single bead is formed.
4. Emulsion PCR is performed to amplify each DNA fragment. By this emulsion PCR, each DNA fragment is clonally amplified in each micro reactor. In this manner, many fragments can be simultaneously and in parallel amplified without competition with other sequences. Subsequently, the emulsion is destroyed and beads bound to amplified DNA fragments are collected.
5. The beads are concentrated and loaded in a pico-titer plate. A single well of the pico-titer plate has a size enough to place a single bead.
6. Four types of nucleic acids (A, C, G and T) are added in a predetermined order to each bead. Pyrophosphoric acid produced during incorporation of each added nucleic acid into the DNA sequence via a polymerase is detected with respect to each bead by a fluorescent reaction of luciferase. Based on the intensity of signal and positional data in combination, the nucleotide sequence is determined.

(4) Step of DNA Typing

Subsequently, after the sff file obtained in the above step (3) is classified depending on MID tags, it is compared with data of known HLA alleles within the nucleotide sequencing database. In this manner, the allele type (6 digits or 8 digits levels) contained in the test sample is determined at the field 3 level or the field 4 level.

In the method of the present invention, typical sets of primers are listed in Table 1 (described above). The present invention is characterized in that primers are designed so as to correspond to the upstream and downstream of exon 2 and exon 3 of each of genes of HLA class II and sandwich these exons and the sequence of the DNA amplified corresponding to almost all regions is determined. In this manner, phase ambiguity (uncertainty) is eliminated and information on a null allele can be obtained.

According to the present invention, since sets of primers for HLA genes are designed so as to anneal at the same temperature during PCR, PCR amplification can be simultaneously performed for a plurality of genes in a single PCR apparatus.

Additionally, owing to the primer sets according to the present invention, a multiplex PCR wherein a plurality of HLA genes are simultaneously PCR amplified in one or two tubes can be performed.

Furthermore, it has been confirmed that sets of primers and enzymes used in the present invention can be applied to a high-speed PCR apparatus. Thus, PCR can be performed more rapidly and accurately than before.

EXAMPLES

The present invention will be more specifically described by way of Examples below; however, the present invention is not limited to these Examples.

Example 1

[Purpose]

The purpose of this example is to check the amplification states for each gene of HLA class II.

[Method]

Using PrimeSTAR® GXL DNA Polymerase (TaKaRa Bio Inc.) as an enzyme, genomic DNA already extracted as a template and primer sets specific to individual HLA class II genes (see Table 1: SEQ ID NOs: 1 to 7), a PCR was carried out. The procedure is more specifically as follows.

(1) To 25 ng of a genomic DNA solution, 4 µL of 5× PrimeSTAR® GXL buffer, 1.6 µL of a dNTP solution, 1 µL of PCR primers (4 pmol/µL) for each and 0.8 µL of PrimeSTAR® GXL polymerase were added. The whole amount of the reaction solution was adjusted to be 20 µL with sterilized water.

(2) After kept at 94° C. for 2 minutes, the preparation of (1) was subjected to a step consisting of a reaction at 98° C. for 10 seconds and a reaction at 70° C. for 3 minutes. This step was repeated 30 times for PCR. Note that, for the PCR amplification, GeneAmp® PCR System 9700 (Life Technologies Corporation) was used. After the PCR, the amplification states of PCR products were checked by an agarose gel electrophoresis method.

[Results and Discussion]

PrimeSTAR® GXL DNA Polymerase was able to PCR amplify HLA genes. The results of performing agarose gel electrophoresis using the PCR amplified products are shown in FIG. 6. It was found that lane 1 was PCR products corresponding to regions including exon 2 and exon 3 of HLA-DRB1, HLA-DRB4 and HLA-DRB5 genes, lane 2 was a PCR product corresponding to a region including exon 2 and exon 3 of an HLA-DQB1 gene, and lane 3 was a PCR product corresponding to a region including exon 2 and exon 3 of an HLA-DPB1 gene. In FIG. 6, lane M represents a DNA size marker. A single PCR amplified product having a desired molecular weight was successfully obtained for each of HLA class II genes by using these primers.

Example 2

[Purpose]

The purpose of this example is to determine the potentiality of a multiplex PCR method of 6 loci of HLA genes including HLA-A, HLA-B and HLA-C genes in addition to HLA class II of Example 1.

[Method]

1. Using PrimeSTAR® GXL DNA Polymerase (TaKaRa Bio Inc.), genomic DNA already extracted from six specimens (Samples 1 to 6 in Table 3) as a template and primer sets specific to individual HLA class I and HLA class II genes (see Table 2: SEQ ID NOs: 8 to 15 and Table 1: SEQ ID NOs: 1 to 7), a PCR was carried out. Note that, the HLA type for each of the six specimens has been already revealed and the specimens include a combination of alleles, in which phase ambiguity was observed in a conventional DNA typing method. The procedure is more specifically as follows.

(1) The PCR was carried out in two 0.2 ml tubes. In short, HLA-A, HLA-B and HLA-C genes were amplified in one of the tubes and HLA-DRB1, HLA-DRB3, HLA-DRB4, HLA-DRB5, HLA-DQB1 and HLA-DPB1 genes were amplified in the other tube.

(2) To 25 ng of a genomic DNA solution, 4 µL of 5× PrimeSTAR® GXL buffer, 1.6 µL of a dNTP solution, 3.2 to 5 µL of PCR primers (10 pmol/µL) for each and 0.8 µL of PrimeSTAR® GXL polymerase were added. The whole amount of the reaction solution was adjusted to be 20 µL with sterilized water.

(3) After kept at 94° C. for 2 minutes, the preparation of (2) was subjected to a step consisting of a reaction at 98° C. for 10 seconds and a reaction at 70° C. for 3 minutes. This step was repeated 30 times for PCR amplification. Note that, for the PCR amplification, GeneAmp® PCR System 9700 (Life Technologies Corporation) was used. After the PCR, the amplification states of PCR products were checked by an agarose gel electrophoresis method.

2. The nucleotide sequences of the PCR products were determined specifically as follows.

(1) A PCR product was purified by MPure XP Kit (Beckman Coulter, Inc.) in accordance with the standard protocol.

(2) The concentration of the purified PCR product was measured by PicoGreen® dsDNA Quantitation Kit (Invitrogen Corp.) in accordance with the standard protocol.

(3) The purified PCR products derived from class I genes and the purified PCR products derived from class II genes were mixed in equal amounts.

(4) A solution of the purified PCR products, a concentration of which was adjusted to be 500 ng/100 µL, was subjected to construction of a rapid library, and then, emulsion PCR and sequencing by GS Junior (Roche) were carried out in accordance with the standard protocol to obtain nucleotide sequences of 15,000 reads per sample.

(5) A search for homology between these nucleotide sequences and known nucleotide sequences of HLA alleles on an IMGT HLA database was performed to select candidate alleles.

(6) The sequences of the candidate alleles were used as a reference. Mapping was performed by GS Reference Mapper (Roche) on condition that the reference matches the read perfectly. The mapping state was checked visually to identify an HLA allele.

[Results and Discussion]

1. The results of performing agarose gel electrophoresis using the PCR amplified products are shown in FIG. 7. In FIG. 7, lanes 1 to 6 correspond to PCR products obtained using Sample ID 1 to Sample ID 6 of Table 3. Lane M represents a DNA size marker. As is evident from FIG. 7, a PCR product and a single PCR amplified product having a desired molecular weight were successfully obtained for each of HLA class I and HLA class II genes in all of the samples by using the primers shown in Tables 1 and 2. Furthermore, the nucleotide sequences of the PCR products were determined by the Sanger method. As a result, HLA alleles were obtained in consistent with known documents. Accordingly, DNA typing of HLA genes can be performed by the PCR system using the primers shown in Tables 1 and 2.

2. Using six specimens containing a combination of alleles, in which phase ambiguity is observed in a conventional DNA typing method, a PCR was performed. PCR products derived from the regions including exon 2 and exon 3 of HLA-A, HLA-B, HLA-C, HLA-DRB1, HLA-DRB3, HLA-DRB4, HLA-DRB5, HLA-DQB1 and HLA-DPB1 genes were subjected to DNA typing of HLA genes by GS Junior. As a result, DNA typing of all of the genes was successfully made at a 6-digit level (Table 3). From this, the method of the present invention can perform DNA typing of HLA genes at a 6-digit or higher level without phase ambiguity and can efficiently detect a substitution, an insertion and a deletion of bases even in introns, which may be causes of a null allele.

mens (Samples 1 to 4 in Table 4) as a template and primer sets specific to individual HLA class I and HLA class II genes (see Table 2: SEQ ID NOs: 8 to 15 and Table 1: SEQ ID NOs: 1 to 5), a PCR was carried out. Note that, the HLA type for each of the four specimens has been already revealed and the specimens include a combination of alleles, in which phase ambiguity was observed in a conventional DNA typing method.

SEQ ID NOs: 8 to 15 of Table 2 and SEQ ID NOs: 1 to 5 of Table 1 were used with respect to HLA-A, HLA-B, HLA-C, HLA-DRB1, HLA-DRB3, HLA-DRB4, HLA-

TABLE 3

| Sample ID | Allele 1 | read | Allele 2 | read | radio |
|---|---|---|---|---|---|
| 1 | A*26 01.01 | 961 | A*31:01:02 | 978 | 0.98 |
|  | B*15:01:01:01 | 996 | B*35:01:01:02 | 966 | 1.03 |
|  | C*03:04:01:02 | 613 | C*07:02:01:04 | 669 | 0.92 |
|  | DRB1*09:01:02:(01) | 1526 | DRB1*13:02:01:(02) | 1929 | 0.79 |
|  | DRB3*03:01:01:(01) | 1675 | DRB4*01:03:02:(01) | 1622 |  |
|  | DQB1*03:03:02:02 | 331 | DQB1*06:04:01:(01) | 244 | 1.36 |
|  | DPB1*02:01:02 | 117 | DPB1*04:01:01 | 120 | 0.98 |
| 2 | A*02:03:01 | 1466 | A*24:02:01:01 | 1419 | 1.03 |
|  | B*38:02:01 | 1134 | B*54:01:01 | 1282 | 0.88 |
|  | C*01:02:01 | 1349 | C*07:02:01:05 | 1421 | 0.95 |
|  | DRB1*04:03:01:02 | 2543 | DRB1*08:03:02:02 | 3773 | 0.67 |
|  | DRB4*01:03:01:(06) | 3664 | — |  |  |
|  | DQB1*03:02:01 | 595 | DQB1*06:01:01 | 536 | 1.11 |
|  | DPB1*13:01 | 484 | DPB1*19:01 | 459 | 1.05 |
| 3 | A*24:02:01:01 | 936 | A*33:03:01 | 948 | 0.99 |
|  | B*44:03:01 | 1219 | B*48:01:01 | 1165 | 1.05 |
|  | C*08:03:01 | 1161 | C*14:03 | 1153 | 1.01 |
|  | DRB1*13:02:01:(02) | 1989 | DRB1*16:02:01:(02) | 1593 | 1.25 |
|  | DRB3*03:01:01:(01) | 1829 | DRB5*02:02:(01):(01) | 584 |  |
|  | DQB1*05:02:01(01) | 316 | DQB1*06:04:01:(01) | 354 | 0.89 |
|  | DPB1*04:01:01 | 119 | DPB1*05:01:01 | 115 | 1.03 |
| 4 | A*02:06:01 | 1178 | A*24:02:01:01 | 1138 | 1.04 |
|  | B*52:01:01:02 | 1278 | B*54:01:01 | 1415 | 0.90 |
|  | C*01:02:01 | 1277 | C*12:02:02 | 1320 | 0.97 |
|  | DRB1*04:05:01:(01) | 2001 | DRB1*15:02:01 | 2290 | 0.87 |
|  | DRB4*01:03:01:(04) | 3175 | DRB5*01:02:(01):(01) | 476 |  |
|  | DQB1*04:01:01:(01) | 468 | DQB1*06:01:01 | 365 | 1.28 |
|  | DPB1*05:01/135:01 | 316 | DPB1*09:01 | 304 | 1.04 |
| 5 | A*24:02:01:01 | 1120 | A*33:03:01 | 1180 | 0.95 |
|  | B*40:02:01 | 448 | B*58:01:01 | 472 | 0.95 |
|  | C*03:02:02:01 | 780 | C*03:04:01:02 | 781 | 1.00 |
|  | DRB1*03:01:01:01/02 | 4071 | DMB1*08:02:01:(01) | 4288 | 0.95 |
|  | DRB3*02:02:(01):(01) | 2563 | — |  |  |
|  | DQB1*02:01:01 | 175 | DQB1*04:02:01:(01) | 433 | 0.40 |
|  | DPB1*02:01:02 | 194 | DPB1*05:01/135:01 | 236 | 0.82 |
| 6 | A*03:02:01 | 2023 | A*24:02:01:01 | 1679 | 1.20 |
|  | B*07:02:01 | 1281 | B*13:02:01 | 1226 | 1.04 |
|  | C*06:02:01:01 | 907 | C*07:02:01:03 | 1028 | 0.88 |
|  | DRB1*01:01:01 | 2022 | DRB1*07:01:01:01 | 2461 | 0.82 |
|  | DRB4*01:03:01:01/03 | 2158 | — |  |  |
|  | DQB1*02:02:01 | 221 | DQB1*05:01:01:(03) | 453 | 0.49 |
|  | DPB1*05:01/135:01 | 301 | DPB1*09:01 | 300 | 1.00 |

*radio = allele1/allele2
*DPB1 shows the number of reads of only exon 2 and exon 3.

Example 3

[Purpose]

The purpose of this example is to determine the potentiality of a multiplex PCR method of 7 loci of HLA genes (HLA-A, HLA-B, HLA-C, HLA-DRB1, HLA-DRB3, HLA-DRB4 and HLA-DRB5 genes) and 9 loci of HLA genes (HLA-A, HLA-B, HLA-C, HLA-DRB1, HLA-DRB3, HLA-DRB4, HLA-DRB5, HLA-DQB1 and HLA-DPB1 genes).

[Method]

1. Using PrimeSTAR® GXL DNA Polymerase (TaKaRa Bio Inc.), genomic DNA already extracted from four speci- DRB5 and HLA-DQB1 genes. DPB1-F2 (5'-CTCAGT-GCTCGCCCCTCCCTAGTGAT-3': SEQ ID NO: 16) and DPB1-R2 (5'-GCACAGTAGCTTTCGGGAATTGACCA-3': SEQ ID NO: 17) were used with respect to an HLA-DPB1 gene. DPB1-F2 (SEQ ID NO: 16) and DPB1-R2 (SEQ ID NO: 17) are represent a set of PCR primers specifically amplifying an HLA-DPB1 gene, which is a β chain of MHC class II. These primers of the set are nucleotide sequences located at positions, which correspond to the upstream and downstream of exon 2 to a 3' untranslated region of an HLA-DPB1 gene and sandwich the region, in a human genome sequence (Reference sequence: hg19). SEQ ID NO: 16 has a nucleotide sequence corresponding to the 33048182nd position to the 33048207th position in a human genome sequence (Reference sequence: hg19). SEQ ID NO: 17 has a complementary nucleotide sequence to a nucleotide sequence corresponding to the 33055428th position to the 33055453rd position in a human genome sequence (Reference sequence: hg19). The length of a PCR product obtained by using this primer set is estimated from the reference sequence as about 7,300 bases (bp).

The procedure is more specifically as follows.

(1) The PCR was carried out in two 0.2 ml tubes. In short, HLA-A, HLA-B, HLA-C, HLA-DRB1, HLA-DRB3, HLA-DRB4 and HLA-DRB5 genes were amplified in one of the tubes. HLA-A, HLA-B, HLA-C, HLA-DRB1, HLA-DRB3, HLA-DRB4, HLA-DRB5, HLA-DQB1 and HLA-DPB1 genes were amplified in the other tube.

(2) To 25 ng of a genomic DNA solution, 4 μL of 5× PrimeSTAR® GXL buffer, 1.6 μL of a dNTP solution, 3.2 to 5 μL of PCR primers (10 pmol/μL) for each and 0.8 μL of PrimeSTAR® GXL polymerase were added. The whole amount of the reaction solution was adjusted to be 20 μL with sterilized water.

(3) After kept at 94° C. for 2 minutes, the preparation of (2) was subjected to a step consisting of a reaction at 98° C. for 10 seconds and a reaction at 70° C. for 3 minutes. This step was repeated 30 times for PCR amplification. Note that, for the PCR amplification, GeneAmp® PCR System 9700 (Life Technologies Corporation) was used. After the PCR, the amplification states of PCR products were checked by an agarose gel electrophoresis method.

2. The nucleotide sequences of the PCR products were determined specifically as follows.

(1) A PCR product was purified by AMPure XP Kit (Beckman Coulter, Inc.) in accordance with the standard protocol.

(2) The concentration of the purified PCR product was measured by PicoGreen® dsDNA Quantitation Kit (Invitrogen Corp.) in accordance with the standard protocol.

(3) The purified PCR products derived from class I genes and the purified PCR products derived from class II genes were mixed in equal amounts.

(4) A solution of the purified PCR products, a concentration of which was adjusted to be 500 ng/100 μL, was subjected to construction of a library, and then, emulsion PCR and sequencing by Ion PGM (Life Technologies Corporation) were carried out in accordance with the standard protocol to obtain nucleotide sequences of 400,000 reads per sample.

(5) A search for homology between these nucleotide sequences and known nucleotide sequences of HLA alleles on an IMGT HLA database was performed to select candidate alleles.

(6) The sequences of the candidate alleles were used as a reference. Mapping was performed by GS Reference Mapper (Roche) on condition that the reference matches the read perfectly. The mapping state was checked visually to identify an HLA allele.

[Results and Discussion]

1. The results of performing agarose gel electrophoresis using the PCR amplified products are shown in FIG. 8. In FIG. 8, lanes 1 to 4 correspond to PCR products obtained using Sample ID 1 to Sample ID 4 of Table 4. The leftmost lane represents a DNA size marker. As is evident from FIG. 8, a PCR product and a single PCR amplified product having a desired molecular weight were successfully obtained for each of genes in all of the samples of both 7 loci of HLA genes and 9 loci of HLA genes by using the primers described above.

2. Using four specimens containing a combination of alleles, in which phase ambiguity is observed in a conventional DNA typing method, a PCR was performed. PCR products derived from each of the genes were subjected to HLA typing by Ion PGM. As a result, DNA typing of all of the genes was successfully made at a 6-digit level (Table 4). From this, the method of the present invention can perform DNA typing of HLA genes at a 6-digit or higher level without phase ambiguity and can efficiently detect a substitution, an insertion and a deletion of bases even in introns, which may be causes of a null allele.

The material in the ASCII text file, named "WING2-56186-SeqLst.txt", created May 24, 2016, file size of 4,096 bytes, is hereby incorporated by reference.

TABLE 4

| sample ID 1 | | sample ID 2 | | sample ID 3 | | sample ID 4 | |
|---|---|---|---|---|---|---|---|
| Allele 1 | Allele 2 | Allele 1 | Allele 2 | Allele 1 | Allele 2 | Allele 1 | Allele 2 |
| Multiplex method of 7 loci of HLA genes | | | | | | | |
| A*03:01:01 | A*31:01:02 | A*02:05:01 | A*03:01:01 | A*11:01:01 | A*32:01:01 | A*11:01:01 | A*23:01:01 |
| B*07:02:01 | B*40:01:02 | B*47:01:01 | B*50:01:01 | B*07:02:01 | B*51:01:01 | B*35:01:01 | B*49:01:01 |
| C*03:04:01 | C*07:02:01 | C*06:02:01 | — | C*07:02:01 | C*15:02:01 | C*04:01:01 | C*07:01:01 |
| DRB1*04:04:01 | DRB1*15:01:01 | DRB1*07:01:01 | — | DRB1*15:01:01 | — | DRB1*04:01:01 | DRB1*10:01:01 |
| DRB4*01:03:01 | | DRB4*01:01:01 | | DRB5*01:01:01 | | DRB4*01:03:01 | |
| DRB5*01:01:01 | | | | | | | |
| Multiples method of 9 loci of HLA genes | | | | | | | |
| A*03:01:01 | A*31:01:02 | A*02:05:01 | A*03:01:01 | A*11:01:01 | A*32:01:01 | A*11:01:01 | A*23:01:01 |
| B*07:02:01 | B*40:01:02 | B*47:01:01 | B*50:01:01 | B*07:02:01 | B*51:01:01 | B*35:01:01 | B*49:01:01 |
| C*03:04:01 | C*07:02:01 | C*06:02:01 | — | C*07:02:01 | C*15:02:01 | C*04:01:01 | C*07:01:01 |
| DRB1*04:04:01 | DRB1*15:01:01 | DRB1*07:01:01 | — | DRB1*15:01:01 | — | DRB1*04:01:01 | DRB1*10:01:01 |
| DRB4*01:03:01 | | DRB4*01:01:01 | | DRB5*01:01:01 | | DRB4*01:03:01 | |
| DRB5*01:01:01 | | | | | | | |
| DQB1*03:02:01 | DQB1*06:02:01 | DQB1*02:02:01 | — | DQB1*06:02:01 | — | DQB1*03:02:01 | DQB1*05:01:01 |
| DPB1*04:01:01 | — | DPB1*04:01:01 | DPB1*15:01 | DPB1*04:01:01 | DPB1*10:01 | DPB1*02:01:02 | DPB1*04:01:01 |

The invention claimed is:

1. A method for DNA typing of a plurality of HLA genes from a human genomic sequence at a six-digit or higher level, comprising the following steps:

(1) a step of preparing a set of primers for at least three target genes from the human genome sequence comprising (1) a first target gene comprising one or more of HLA-DRB1, HLA-DRB3, HLA-DRB4, or HLA-DRB5, (ii) a second target gene comprising HLA-DQB1, and (iii) a third target gene comprising HLA-DPB1, wherein the primers anneal specifically to an intron 1 and an exon 4 region, respectively, of each of the three target genes, and amplify a region comprising exon 2, intron 2, exon 3, intron 3, and a part of exon 4 of each of the three target genes;

wherein the set of primers comprises oligonucleotides having nucleotide sequences as shown in SEQ ID NOs: 1 and 2, respectively, for amplifying the region of the first target gene;

wherein the set of primers comprises oligonucleotides having nucleotide sequences as shown in any one of SEQ ID NOs: 3 or 4, or both, and SEQ ID NO: 5, respectively, for amplifying the region of the second target gene; and wherein the set of primers comprises oligonucleotides having nucleotide sequences as shown in SEQ ID NOs: 6 and 7, respectively, for amplifying the region of the third target gene;

(2) a step of PCR amplifying a test sample (DNA) using the set of primers in a multiplex PCR method to obtain PCR amplified products of each of the at least three target genes;

(3) a step of determining the nucleotide sequences of the PCR amplified products; and (4) optionally, a step of carrying out a homology search within a database.

* * * * *